United States Patent
Shanley

(10) Patent No.: US 9,724,079 B2
(45) Date of Patent: Aug. 8, 2017

(54) SYSTEM AND METHOD FOR PROVIDING ACCESS AND CLOSURE TO TISSUE

(75) Inventor: John F. Shanley, Emerald Hills, CA (US)

(73) Assignee: ENTOURAGE MEDICAL TECHNOLOGIES, INC., Menlo Park, CA (US)

( * ) Notice: Subject to any disclaimer, the term of this patent is extended or adjusted under 35 U.S.C. 154(b) by 0 days.

(21) Appl. No.: 12/942,939

(22) Filed: Nov. 9, 2010

(65) Prior Publication Data

US 2011/0190811 A1  Aug. 4, 2011

Related U.S. Application Data

(60) Provisional application No. 61/259,636, filed on Nov. 9, 2009.

(51) Int. Cl.
| | | |
|---|---|---|
| A61B 17/08 | (2006.01) | |
| A61B 17/00 | (2006.01) | |
| A61B 17/064 | (2006.01) | |
| A61B 17/34 | (2006.01) | |

(52) U.S. Cl.
CPC ... *A61B 17/0057* (2013.01); *A61B 2017/00243* (2013.01); *A61B 2017/00247* (2013.01); *A61B 2017/00575* (2013.01); *A61B 2017/00623* (2013.01); *A61B 2017/0649* (2013.01); *A61B 2017/3425* (2013.01); *A61B 2017/3488* (2013.01)

(58) Field of Classification Search
CPC ...... A61B 17/0057; A61B 2017/00575; A61B 2017/00247; A61B 2017/0649
See application file for complete search history.

(56) References Cited

U.S. PATENT DOCUMENTS

| | | | |
|---|---|---|---|
| 4,204,541 | A | 5/1980 | Kapitanov |
| 4,641,652 | A | 2/1987 | Hutterer et al. |
| 5,356,424 | A | 10/1994 | Buzerak et al. |
| 5,665,109 | A | 9/1997 | Yoon |
| 5,782,844 | A | 7/1998 | Yoon et al. |

(Continued)

FOREIGN PATENT DOCUMENTS

| | | |
|---|---|---|
| CN | 1997318 A | 7/2007 |
| WO | 2005/102181 | 11/2005 |

(Continued)

OTHER PUBLICATIONS

PCT International Search Report and Written Opinion for PCT/US2010/056084, Applicant Entourage Medical Technologies, LLC., Forms PCT/ISA/210, 220, 237, dated May 16, 2011 (11 pages).

(Continued)

*Primary Examiner* — Todd J Scherbel
(74) *Attorney, Agent, or Firm* — Vista IP Law Group, LLP

(57) ABSTRACT

Embodiments are described for creating and closing tissue access ports or defects, such as transapical access ports, which involve placement of an elongate prosthesis in a helical configuration across the tissue structure site to be crossed, and confirmation that such helical suture configuration is positioned appropriately, before further interventional steps. A plug member may be included to assist with closure of the ports of defects. The elongate prosthesis and plug member may comprise bioresorbable materials.

26 Claims, 13 Drawing Sheets

(56) References Cited

U.S. PATENT DOCUMENTS

| | | | |
|---|---|---|---|
| 6,663,633 B1* | 12/2003 | Pierson, III | 606/148 |
| 7,104,949 B2* | 9/2006 | Anderson et al. | 600/30 |
| 7,695,432 B2 | 4/2010 | Scheyer | |
| 8,696,689 B2 | 4/2014 | Tuval et al. | |
| 9,044,267 B2 | 6/2015 | Litvack et al. | |
| 2003/0055313 A1 | 3/2003 | Anderson et al. | |
| 2004/0030382 A1 | 2/2004 | St. Goar et al. | |
| 2004/0220596 A1 | 11/2004 | Frazier et al. | |
| 2005/0021057 A1 | 1/2005 | St. Goar et al. | |
| 2005/0187568 A1 | 8/2005 | Klenk et al. | |
| 2005/0267524 A1 | 12/2005 | Chanduszko | |
| 2006/0200199 A1 | 9/2006 | Bonutti et al. | |
| 2006/0282088 A1* | 12/2006 | Ryan | 606/144 |
| 2006/0287661 A1 | 12/2006 | Bolduc et al. | |
| 2007/0032823 A1 | 2/2007 | Tegg | |
| 2007/0049944 A1 | 3/2007 | Stone | |
| 2008/0086168 A1 | 4/2008 | Cahill | |
| 2009/0062839 A1 | 3/2009 | Kurrus | |
| 2009/0240264 A1* | 9/2009 | Tuval et al. | 606/148 |
| 2009/0275960 A1* | 11/2009 | Provenza et al. | 606/144 |
| 2010/0087854 A1* | 4/2010 | Stopek et al. | 606/215 |
| 2010/0256666 A1* | 10/2010 | Chen et al. | 606/191 |
| 2011/0028995 A1* | 2/2011 | Miraki et al. | 606/144 |
| 2012/0059395 A1* | 3/2012 | Kehdy et al. | 606/144 |
| 2012/0116418 A1* | 5/2012 | Belson et al. | 606/139 |
| 2012/0136200 A1 | 5/2012 | Miraki | |
| 2012/0143226 A1* | 6/2012 | Belson et al. | 606/148 |
| 2012/0150223 A1 | 6/2012 | Manos et al. | |

FOREIGN PATENT DOCUMENTS

| | | |
|---|---|---|
| WO | 2007/098212 | 8/2007 |
| WO | 2010/107698 A2 | 9/2010 |

OTHER PUBLICATIONS

"Communication under Rule 71(3) EPC mailed on Dec. 17, 2013", for European Patent Application No. 10779621.1 filed on Nov. 9, 2010, (6 pages).

* cited by examiner

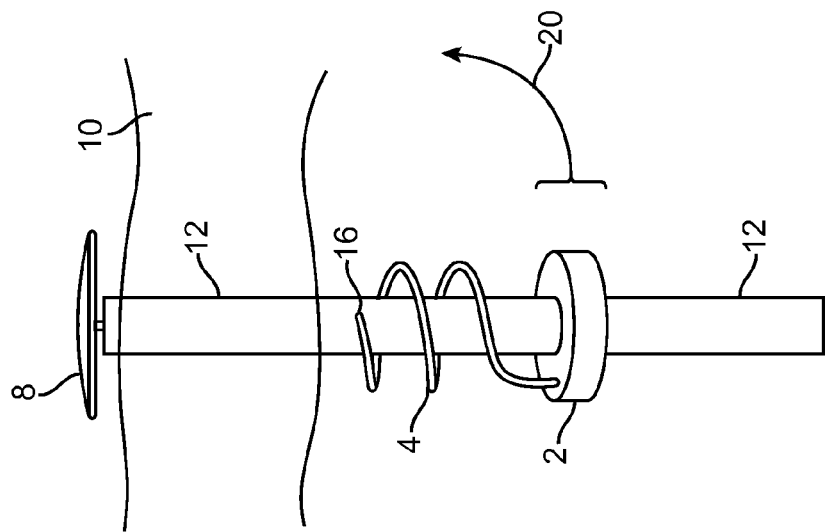
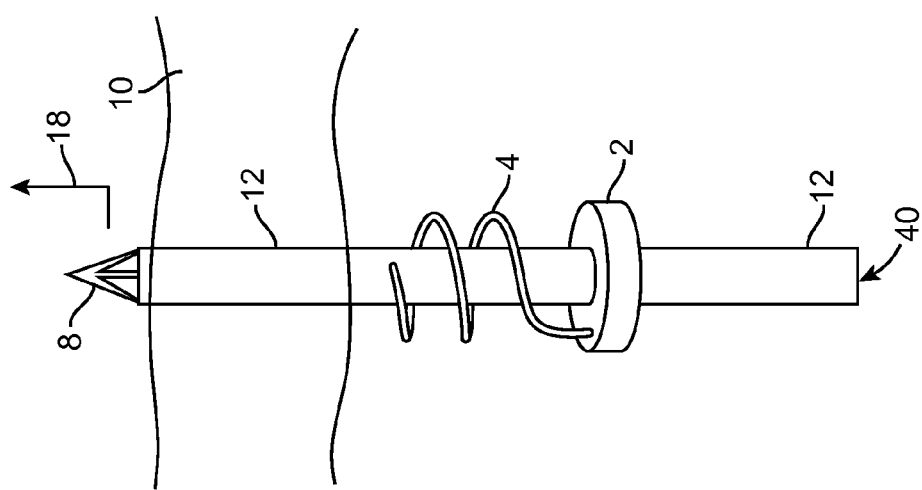

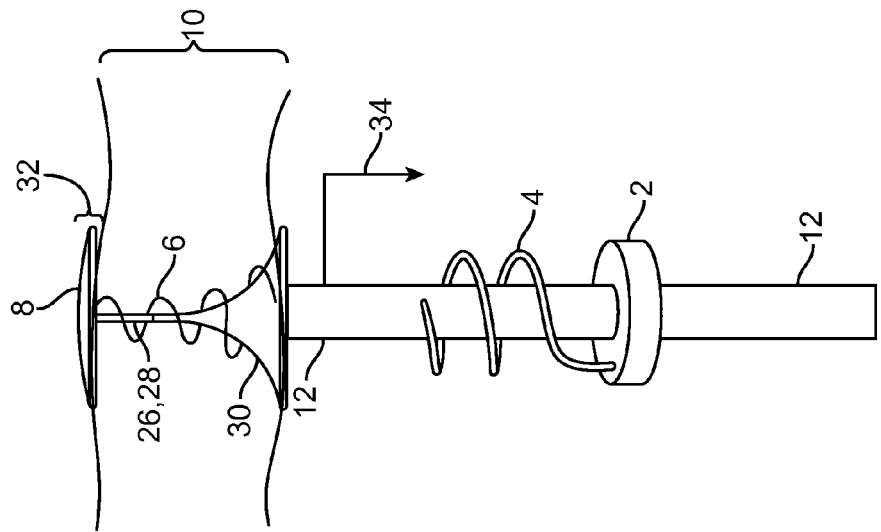
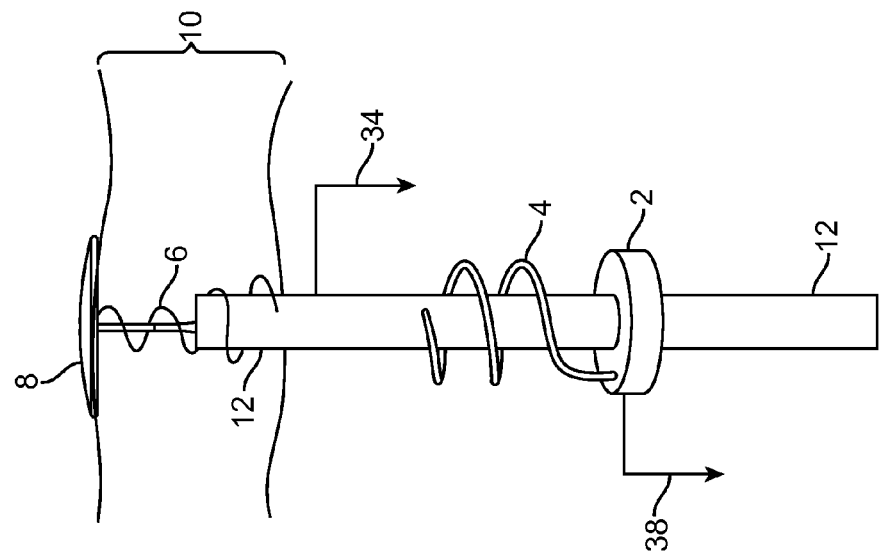
FIG. 3J
FIG. 3K

SYSTEM AND METHOD FOR PROVIDING ACCESS AND CLOSURE TO TISSUE

RELATED APPLICATION DATA

The present application claims the benefit under 35 U.S.C. §119 to U.S. provisional patent application Ser. No. 61/259,636, filed Nov. 9, 2009. The foregoing application is hereby incorporated by reference into the present application in its entirety.

FIELD OF THE INVENTION

The present invention relates generally to devices and methods for performing surgical procedures, and more specifically to access and closure technologies pertinent to wound or defect closure, such as closures required following transapical or transventrical cardiac diagnostic and interventional procedures.

BACKGROUND

Minimally invasive diagnostic and interventional procedure prevalence in US and foreign hospitals continues to increase, as does the demand for certain procedures which involve placement of relatively large devices into targeted locations within tissue structures of criticality. Procedures such as aortic valve replacement conventionally have been addressed with open surgical procedures which are highly invasive. More recently, such procedures have been attempted using natural lumen (i.e., through large blood vessels after an initial surgical transcutaneous or percutaneous access to such vessels) access and delivery systems. Referring to FIG. 1, such systems typically are configured, for example, to reach the aortic valve (112) location inside of the heart (102) from an antegrade approach, which generally requires navigating instrumentation through three of the four chambers of the beating heart (the right atrium 122, left atrium 108, and left ventricle 120, by way of the mitral valve 110 and atrial septum), or from a retrograde approach, which generally requires navigating instrumentation along the aortic arch, from the descending aorta (104) to the ascending aorta (106) and adjacent the aortic valve (112). Each of these approaches presents certain clinical challenges to the surgical team, some of which may be avoided by using what is referred to as a transapical approach, whereby the surgeon creates transcutaneous access to the region around the apex of the heart (126) with a surgical thoracotomy, followed by direct access to the left ventricle (120) using a needle or other device aimed to access the left ventricle (120) around the left ventricular apex (124), which may be followed by one or more dilating instruments to create a temporary access port to the left ventricle. Aspects of a conventional access procedure are illustrated in FIG. 2, wherein a needle device (134) is puncturing the muscular heart wall (130) to gain access to the left ventricle (120) around the location of the left ventricular apex (124). Also shown is a guidewire (136) which may be advanced (38) toward and through the aortic valve (112) to assist with diagnostic and interventional aspects of the procedure. Using these and other instruments such as dilators, this left ventricular access port may be utilized, for example, to replace an aortic valve if bleeding and tissue damage around the access port can be successfully mitigated during such procedure. Subsequent to such a procedure, the instrumentation needs to be removed and the access port closed, usually leaving a prosthetic valve or portion thereof behind. The successful closure of a transapical wound on a beating heart of a patient is obviously of high criticality to such a procedure, as is the minimization of loss of blood. Conventional transapical closure techniques typically involve the placement of small sutures to create a purse-string type effect to close the wound as the instrumentation is withdrawn, and it may be very difficult to repeatably create acceptable closures using these techniques without a larger thoracotomy or improved instrumentation. In other words, one of the key challenges to transapical intervention remains transapical wound closure. Indeed, it is believed that transapical access may provide enhanced stability and control during procedures such as aortic valve replacement, due to the fact that the operator may have a relatively direct mechanical connection with the pertinent instrumentation, relative to the connection that he may have using, for example, an antegrade or retrograde vascular approach with more compliant catheter type tools. For this reason, it is even more desirable to successfully address the challenges of transapical access and closure. Further, it would be desirable to have a wound or access closure technology that was applicable not only to transapical access port closure, but also other closure demands pertinent to other surgical interventions of the human body wherein wounds or ports are created, such as in gastrointestinal or gynecological surgery.

BRIEF DESCRIPTION OF THE DRAWINGS

FIGS. 3A to 3L illustrate various aspects of a closure configuration wherein a helical tubular member may be utilized to deploy an elongate prosthesis such as a suture or coil.

SUMMARY OF THE INVENTION

Figure 1:
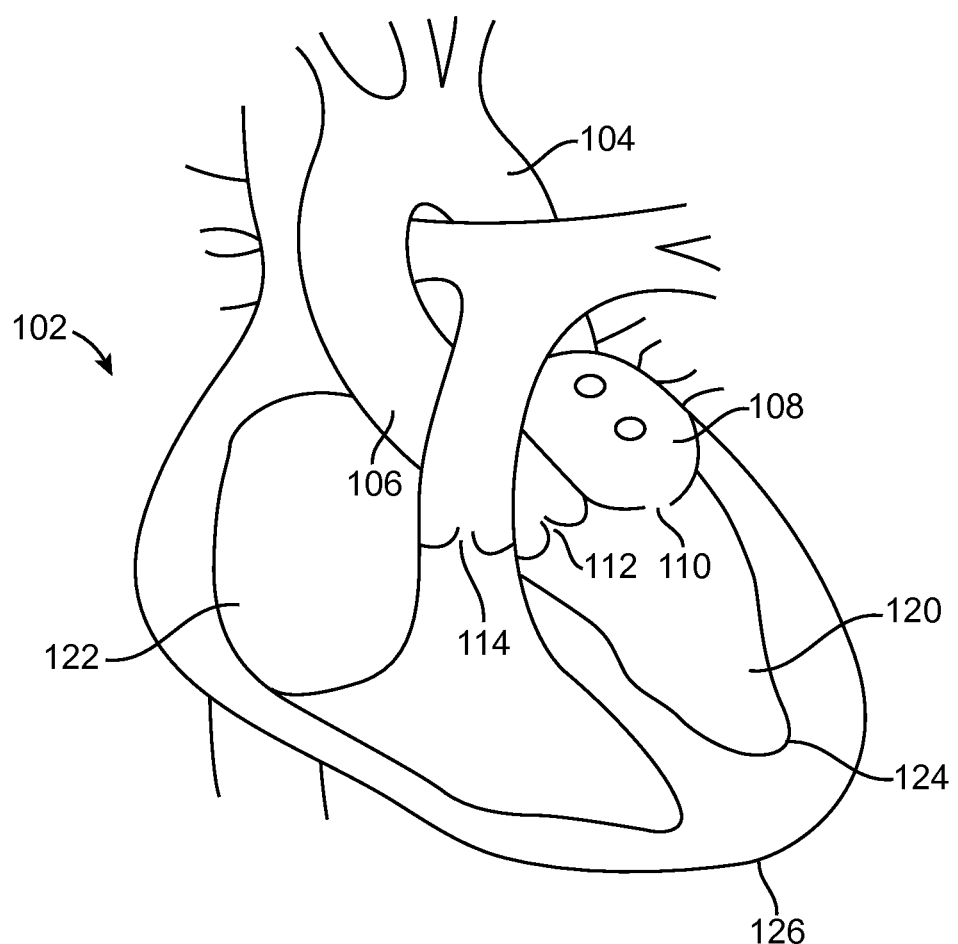
FIG. 1 illustrates aspects of the human heart anatomy.
Figure 2:
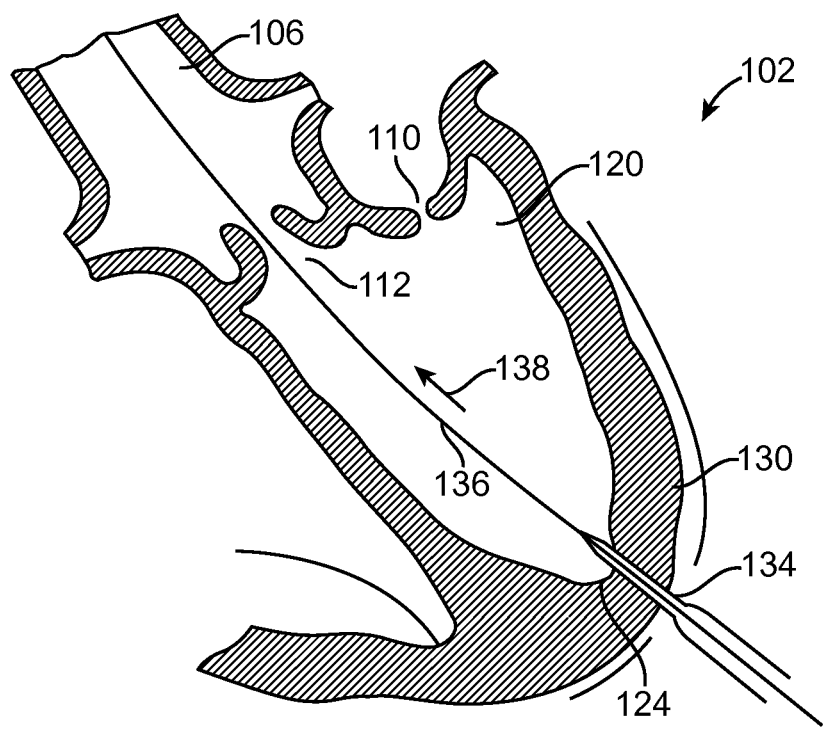
FIG. 2 illustrates a conventional transapical access procedure.

One embodiment is directed to a system for closing a defect in a tissue wall, comprising: a base member having a proximal end and a distal end, the proximal end being configured to be manually manipulated by an operator; a helical tubular member having a proximal end, a distal end, a longitudinal axis, and a helical length in between the proximal and distal ends, the helical tubular member defining a helical lumen therethrough, wherein the proximal end is coupled to the base member and the distal end defines a distal outlet of the helical lumen; and an elongate prosthesis coupled to the helical tubular member along two or more portions of the helical length and configured to be deployed into a portion of the tissue wall when decoupled from the helical tubular member; wherein the helical tubular member is configured to be helically advanced into an advanced position in the tissue wall with the defect substantially aligned with the longitudinal axis of the helical tubular member, and to decouple from the elongate prosthesis upon helical retraction, leaving the elongate prosthesis behind in a deployed helical configuration similar to that previously defined by the helical advanced position of the helical tubular member, the deployed configuration being selected to retain coaptation of the defect. The system may further comprise a plug member having an elongate central portion, the plug member insertable into the defect in the tissue wall and configured to span at least a portion of a depth dimension of the defect in the tissue wall and place at least a portion of the tissue wall adjacent the defect into a constrained configuration in between the plug member and portions of the deployed helical configuration of the elongate prosthesis. The base member comprises an elongate shaft. The base member may define a hole therethrough, the hole configured to facilitate a movable coupling between the base member and an elongate instrument selected from the group consisting of: a catheter, a cannula, a dilator, a needle, a guidewire, and an elongate probe. The helical tubular member may have a tubular outer diameter (i.e., the diameter of the overall helical construct) between about 1 mm and about 25 mm. The helical tubular member may have a helical lumen diameter (i.e., the inner diameter of the helical tubular member material) between about 10 thousandths of an inch and about 80 thousandths of an inch; the outer diameter of the helical tubular member material may be between about 30 thousandths of an inch and about 100 thousandths of an inch. The helical tubular member may have a helical winding pitch between about 1 mm and about 10 mm. The helical tubular member distal end may comprise a cutting tip. The helical tubular member may comprise a metal or polymer material. The helical tubular member may comprise a helically-bent section of metal hypotube. The elongate prosthesis may comprise an unloaded three dimensional shape that is different from the shape of the helical lumen. The unloaded three dimensional shape may substantially approximate a line. The unloaded three dimensional shape may comprise a helical shape having a circular section diameter that is less than that of the helical lumen. The elongate prosthesis may be highly flexible into a plurality of unloaded three dimensional shape configurations. The elongate prosthesis may comprise an element selected from the group consisting of: a suture, a wire, and a linkage. The elongate prosthesis may comprise a material selected from the group consisting of: a metal, a non-bioresorbable polymer, a bioresorbable polymer, a non-bioresorbable co-polymer, and a bioresorbable co-polymer. The elongate prosthesis further may comprise a distal anchor. The distal anchor may comprise an element selected from the group consisting of: a knot, a barb member, and a catch geometry. The plug member may comprise a distal portion coupled to the distal end of the central portion, and a proximal portion coupled to the proximal end of the central portion, each of the proximal and distal portions being expandable from a collapsed configuration to an expanded configuration such that the outer diameter of each collapsed configuration is larger than that of the central portion. The plug member central portion may comprise a substantially cylindrical geometry. The plug member may comprise a material selected from the group consisting of: a metal, a non-bioresorbable polymer, a bioresorbable polymer, a non-bioresorbable co-polymer, a bioresorbable co-polymer, and a fabric.

DETAILED DESCRIPTION

Figure 3B:
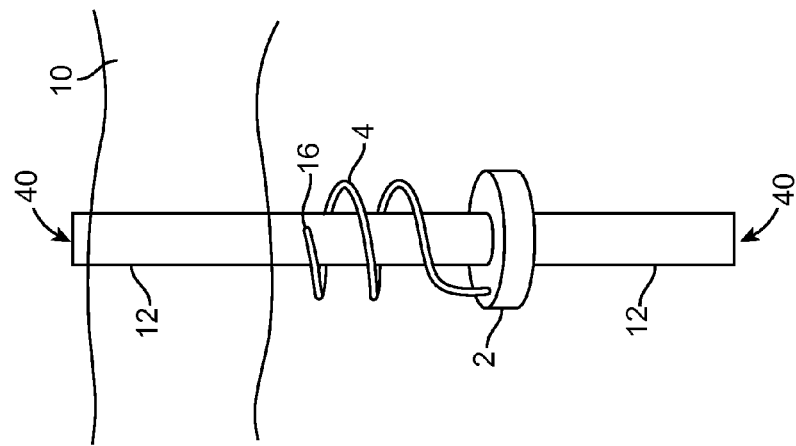
Figure 3A:
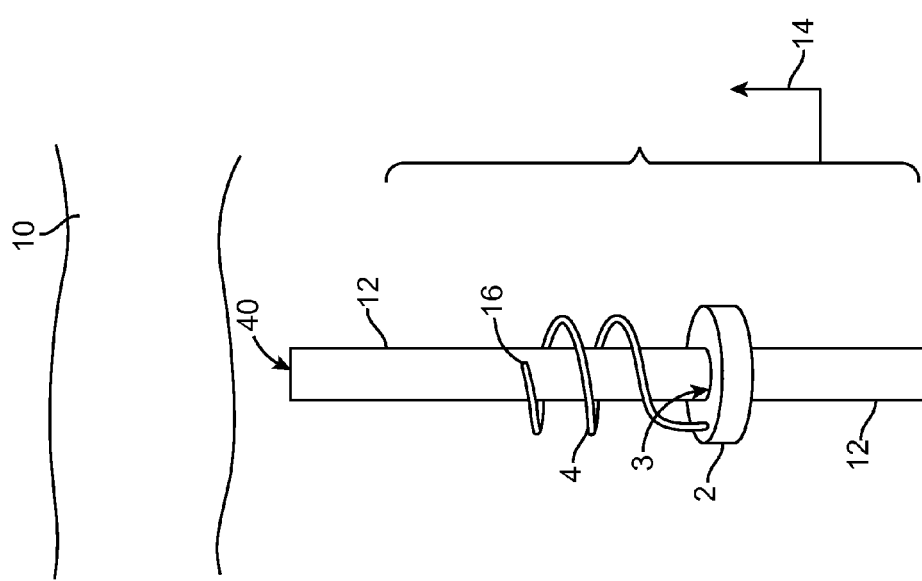

Referring to FIGS. 3A through 3L, various aspects of embodiments associated with a transapical access and closure system are depicted. These same configurations may be applied to various other cardiovascular and noncardiovascular tissue wall defect or port closure scenarios. As shown in FIG. 3A, an assembly comprising an elongate member, such as a catheter defining a working lumen (40) therethrough, a cannula, or other elongate instrument or probe, is advanced (14) toward a subject tissue wall (10), in this example a portion of the myocardium. The elongate member (12) may comprise a hemostatic valve. The assembly also comprises a base member (2) movably coupled to the elongate member (12) via a hole or annulus (3) created through the middle of the base member (2) to accommodate one or more elongate tools such as the elongate member (12) shown. The base member preferably is configured to be manually manipulated in insertion/retraction and also rotation and may comprise an elongate shape itself (for example, such as a catheter or hypotube structure) to facilitate manual manipulation from an extracorporeal location by an operator; for illustration a simple embodiment is shown wherein the base member (2) comprises a relatively thin cylindrical shape. The depicted assembly also comprises a helical tubular member (4) or "spring insertion device" with a proximal end coupled to the base member (2) and a distal end having a cutting tip configured to readily dive into the subject tissue structure with helical advancement (i.e., in a corkscrew type fashion) of the base member (2) and helical tubular member (4). The cutting tip (16) may comprise a sharpened end of the helical tubular member (4), or may comprise a sharpened fitting coupled to the helical tubular member (4). The helical tubular member (4) may comprise a metal or polymer material, and in one embodiment comprises a helically bent or wrapped section of metal hypotube defining a lumen therethrough which may be utilized for deployment of an elongate prosthesis member or "helical spring", as described below.

Referring to FIG. 3B, a distal portion of the elongate member (12) has been advanced across at least a portion of the subject tissue wall (10), in this example across the entire thickness of the wall (10) to facilitate a procedure such as an aortic valve replacement wherein the working lumen (40) of the depicted elongate member (12) may be utilized as a conduit for passing various tools and prosthesis portions. FIG. 3B depicts an embodiment wherein the helical tubular member (4) has not been advanced into or across the tissue wall (10) yet, and such a configuration may be utilized to facilitate a valve replacement or other procedure. In another embodiment, as described below, for example, in reference to FIGS. 4C and 4D, the helical tubular member (4) indeed may be advanced across at least a portion of the tissue wall (10) before utilizing the working lumen (40) for the interventional procedure, to ensure that a closure scenario is nearly fully in place before the intervention begins.

Referring to FIG. 3C, after the use of the working lumen of the elongate member (12) for any interventional procedure is complete and a closure is desired, a collapsible and/or pliable sealing device or plug member (8) may be inserted through the hemostatic valve and working lumen (40) of the elongate member (12) and allowed to partially expand to its natural shape, as shown in FIG. 3D wherein the distal or top portion of the plug member (8) has expanded outward. Also, the assembly of the base member (2) and helical tubular member (4) may be helically advanced (20) may be advanced into the tissue wall, as shown in FIG. 3E.

Figure 3F:
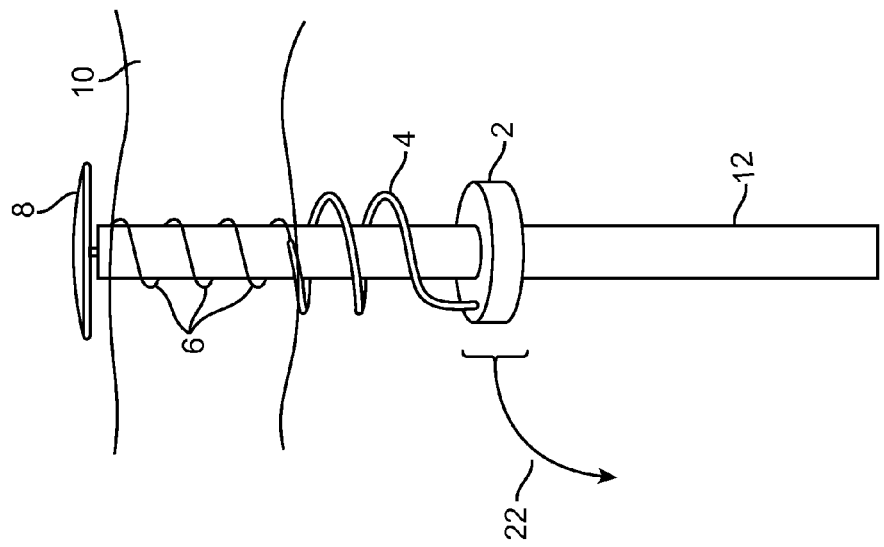
Figure 3E:
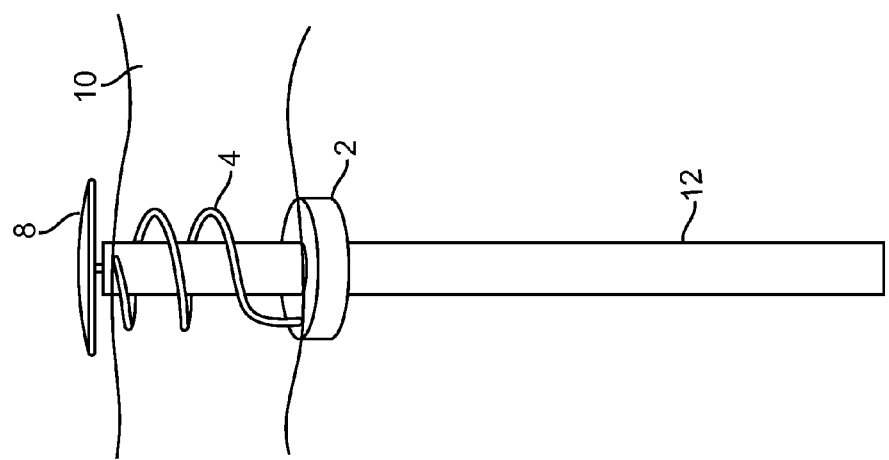
Figure 3H:
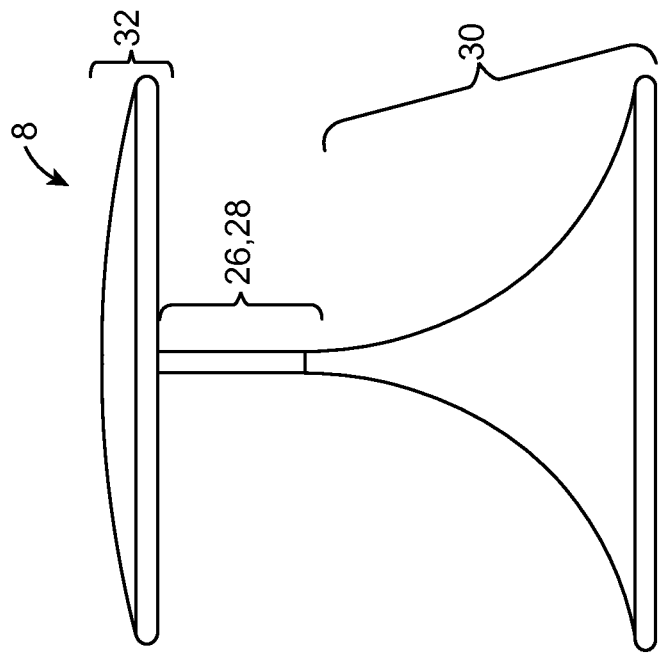

Referring to FIG. 3F, with helical retraction (22) of the assembly of the base member (2) and helical tubular member (4), an elongate prosthesis (6), is decoupled and left behind in the tissue wall (10) a helical or coiled configuration. In the views illustrated in FIGS. 3A-3E, the elongate prosthesis (6) preferably has been located within a small lumen defined by the helical tubular member (4), and upon reversing the helical advancement to helical retraction, the elongate prosthesis (6) is configured to be pulled out of the helical tubular member (4) and left in place. A distal end of the elongate prosthesis (6) may comprise an anchor, such as a knot tied in the material or the elongate prosthesis (6), a barb coupled to or formed into the elongate prosthesis (6), or other catch member such as a hook, burr, or toggle bolt anchor structure. The elongate prosthesis may naturally have an unloaded three dimensional shape that is different than that of the helical tubular member (4). For example, in one embodiment, the unloaded three dimensional shape may substantially approximate a line—as in a piece of unloaded straight wire sitting on a tabletop. In the embodiment depicted in FIGS. 3F, and 3J-3L, the elongate prosthesis (6) has helical unloaded three dimensional shape that has a helical diameter smaller than that of the helical tubular member (4), such that when the elongate prosthesis (6) is released from the lumen of the helical tubular member (4), it tends to apply a mild constricting load (a mild uniform radial compression) on tissue trapped between the elongate prosthesis and the central axis of the tubular member (12), or the central axis of the elongate prosthesis helix. Thus in the configuration shown in FIG. 3F, the elongate prosthesis (6) is constricting the trapped tissue toward the outer surface of the tubular member (12). In FIGS. 3J-3L, the elongate prosthesis (6) is constricting the trapped tissue toward the outer surface of the deployed plug member (8) and/or tubular member (12) outer surface that remains adjacently positioned. The elongate prosthesis (6) may comprise a suture, wire, coil, or linkage made from one or more metals, polymers, co-polymers, or fabrics. The polymers may be bioresorbable. The elongate prosthesis (6) may be very thin and/or highly flexible as an overall construct such that it may be configured into a variety of unloaded three dimensional shape configurations.

Figure 3G:
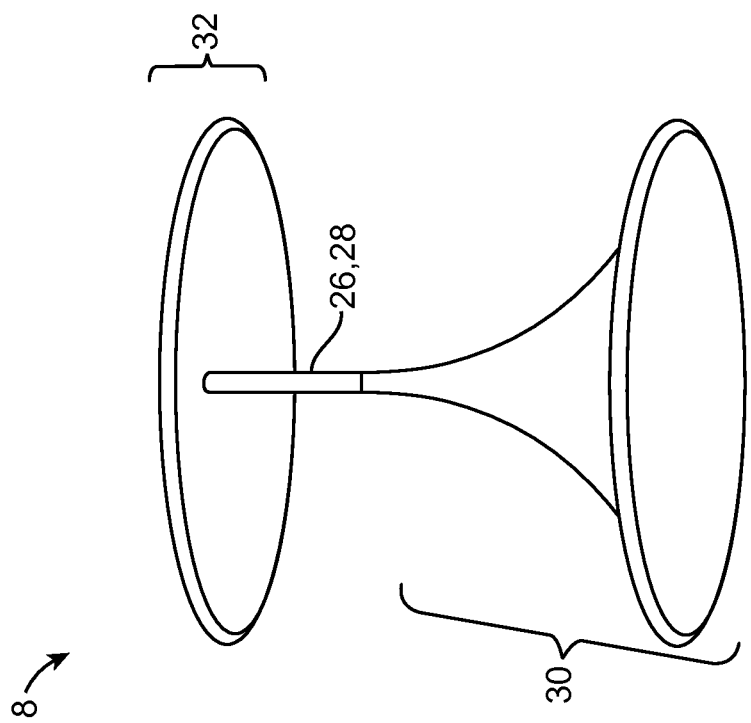
Figure 3I:
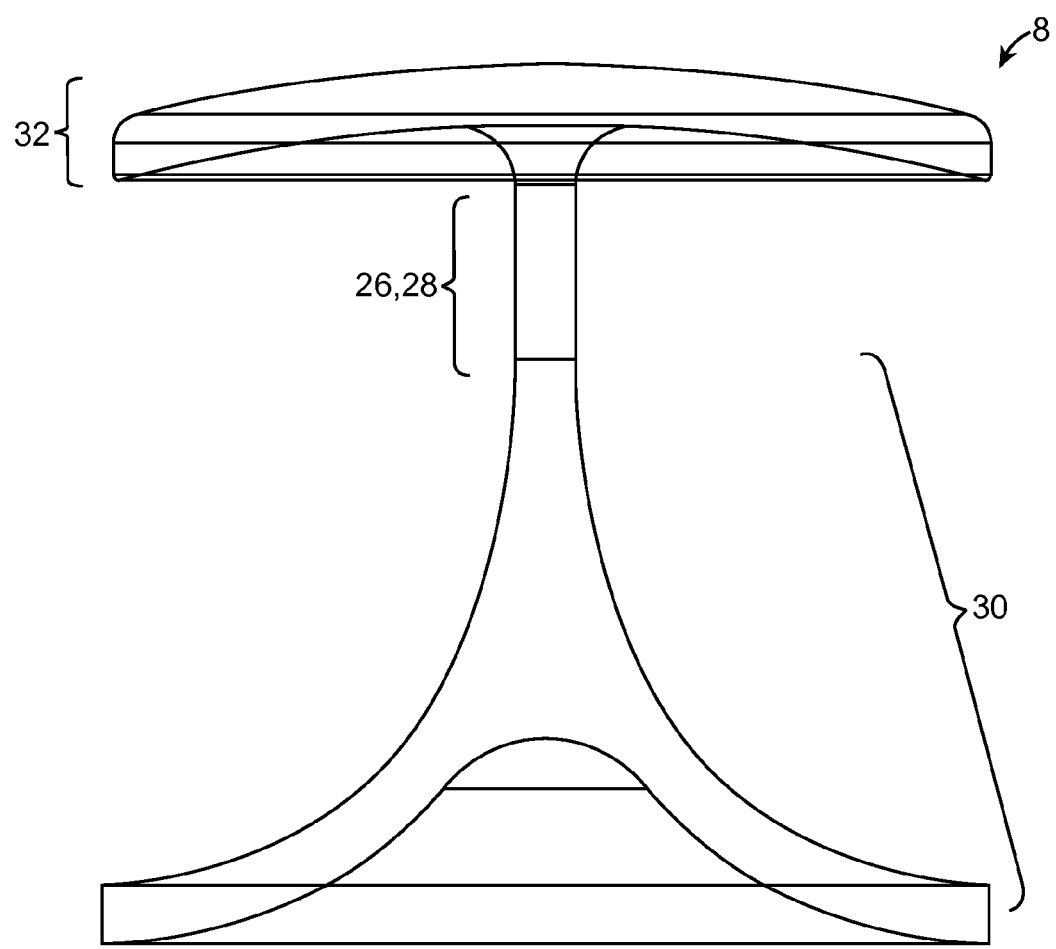
Figure 3L:
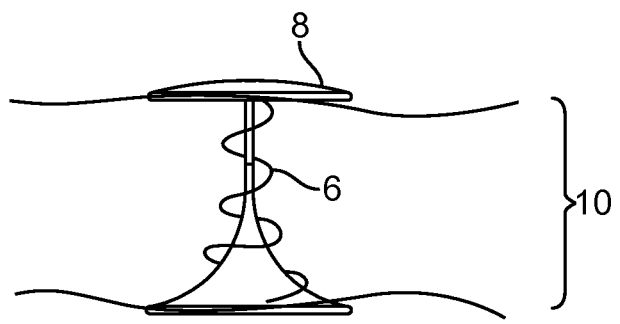
Figure 3L:
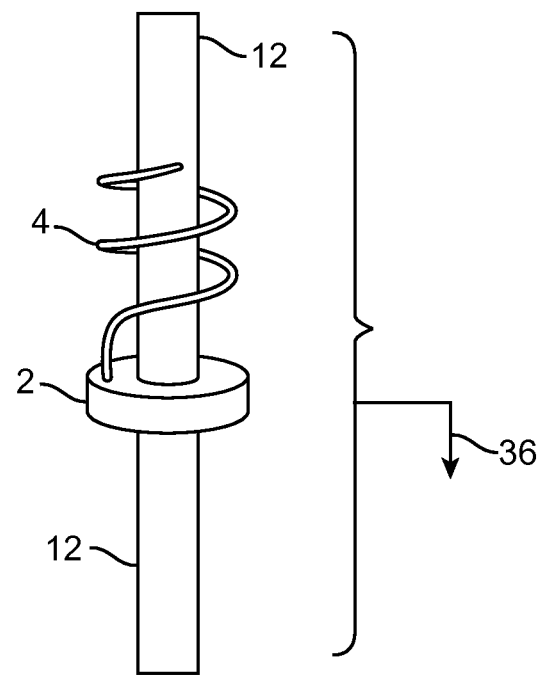

Referring to FIG. 3G, a close-up orthogonal view of one embodiment of an expandable plug member (8) is shown. A central portion (26), which may be substantially cylindrical (28) in shape, may serve as a coupling between a concave expandable distal portion (32) and an arcuate conical proximal portion (30). Such a plug member (8) may comprise one or more metals, polymers, co-polymers, fabrics, or foams. The polymers may be bioresorbable. Preferably such a plug member (8) may be folded or collapsed to a substantially small cylindrical geometry for delivery through a working lumen, as shown, for example, in FIG. 3C. Other views of an expandable plug member (8) are shown in FIGS. 3H and 3I.

Referring to FIG. 3J, to further complete the illustrated defect closure process, the elongate member (12) is further withdrawn (34), as is the base member (2) further withdrawn (38). With the increased withdrawal (34) of the tubular member (12), more of the expandable plug member (8) is allowed to expand out of the distal end of the elongate member (12) until it is fully expanded, as shown in FIG. 3k. The deployed elongate prosthesis (6) continues to urge captured tissue against the outer surface of the fully deployed expandable plug member (8), causing a hemostatic closure of the defect. Referring to FIG. 3L, the assembly of the elongate member (12), base member (2), and helical tubular member (4) is withdrawn (36) away from the surgical theater, leaving behind a hemostatic closure configuration of the elongate prosthesis (6) and the plug member (8).

In a defect closure scenario wherein the tissue structure (10) illustrated in FIGS. 3A-3L is a myocardial wall, the radial forces applied by the deployed elongate prosthesis generally apply no axial force to the plug member (8) in the region of the relatively straight central portion (26) of the plug member (8), and preferably this central portion (26) is relatively thin, which may allow the myocardial tissue to almost completely close. Radial forces from the arcuate conical portion (30) have an unresolved axial component in the proximal direction (i.e., tending to pull against the upper concave portion (32). Such a loading configuration will have the effect of pulling the inner seal or concave portion (32) tighter against the inner wall of the heart cavity, and natural contractile motion of the heart may act in concert with the elongate prosthesis, or "spring member", forces, possibly providing a beneficial seal-tightening action with additional heartbeats. Preferably such a deployed configuration distributes closure stresses more evenly on local tissues than does a conventional suture-based closure.

While the illustrative embodiments of FIGS. 3k and 3L depict the plug member (8) and/or elongate prosthesis (6) spanning approximately the full thickness of the depicted tissue wall (10), in other embodiments it is desirable to have one or both ends of each of these structures (8, 6) ultimately positioned midsubstance (i.e., not immediately adjacent a border of the tissue structure 10). Further, while the embodiments depicted in FIGS. 3K and 3L show the plug member (8) and elongate prosthesis (6) substantially aligned longitudinally (i.e., lengthwise along a longitudinal central axis of either member) as well as axially (i.e., about a longitudinal central axis of either member), in other embodiments, it is desirable to have either longitudinal misalignment, axial misalignment, or both, to facilitate stable hemostasis. For example, in one embodiment, it is desirable to have the proximal portion of the elongate prosthesis helically extend proximally beyond the bottom/proximal margin of the arcuate conical portion (30) of the plug member. In other embodiments, a non-expandable plug member may be used in place of the structurally collapsible/expandable plug member (8) shown in FIGS. 3C-3L. For example, in one embodiment, a simple cylindrical plug member sized to be slightly less in diameter than the inner diameter of the elongate member (12), to facilitate pushability through the elongate member (12) during deployment, may be utilized; such a nonexpanding plug member may comprise a relatively compliant, or relatively noncompliant, polymer, such as a bioresorbable polymer.

Figure 4A:
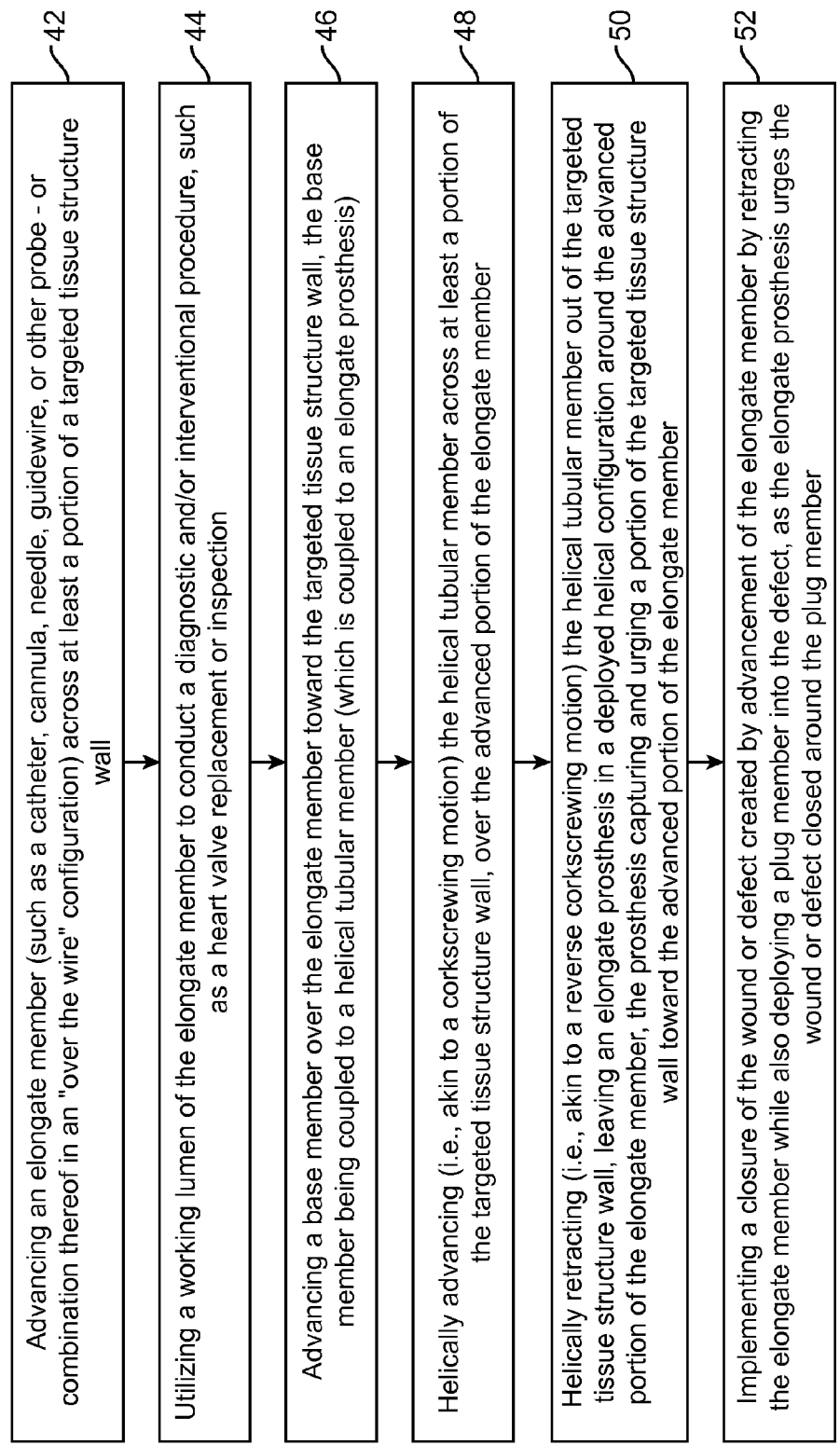
FIGS. 4A-4D depict techniques for implementing various embodiments of the subject helical closure configurations.

Referring to FIG. 4A, one embodiment of deployment process is illustrated. In this embodiment, an elongate member, such as a catheter, cannula, needle, guidewire, or other probe, is advanced across at least a portion of a targeted tissue structure (41). This advancement may employ successive tools, as in an "over-the-wire" procedure wherein a needle and/or guidewire may serve as pathway predecessors for a larger instrument such as a catheter or cannula. As shown in FIG. 4A, a working lumen of the installed elongate member may be utilized to conduct a diagnostic and/or interventional procedure, such as a heart valve inspection or replacement (44). In the illustrated embodiment, next a base member coupled with a helical tubular member may be advanced toward the tissue structure, the helical tubular member preferably carrying with it (i.e., threaded through at least a portion of the helical lumen of the helical tubular member) an elongate prosthesis (46). The helical tubular member may be helically advanced into the targeted tissue structure, over the elongate member (48), then helically retracted (50) to leave the elongate prosthesis in place, preferably urging at least a captured portion of the tissue structure toward the outer surface of the remaining elongate member (i.e., and generally toward the longitudinal axis of the helically deployed elongate prosthesis). Finally the wound or defect may be closed with removal of the elongate member and deployment of a plug member (52), as shown in FIGS. 3C-3L.

Figure 4B:
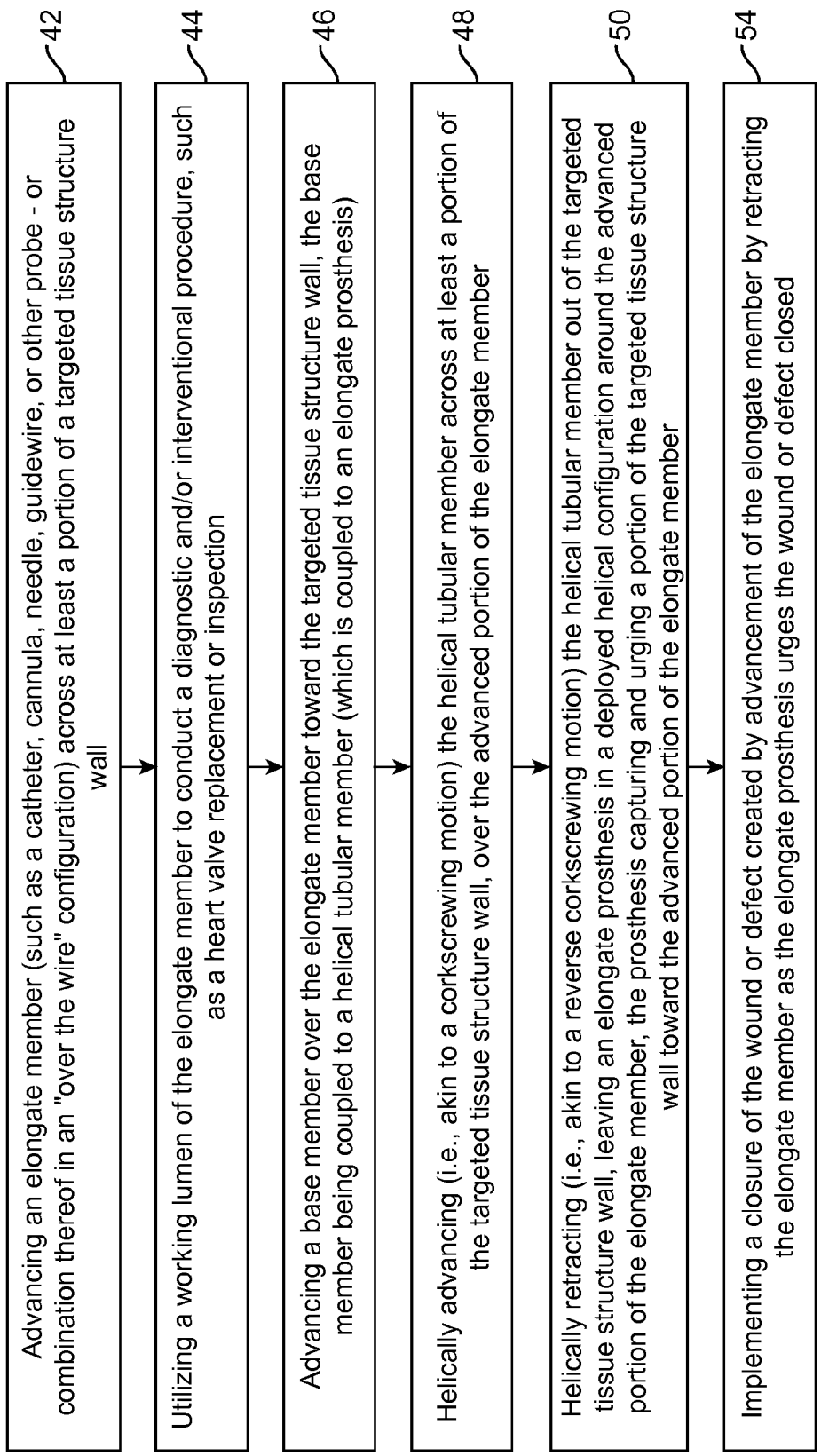

Referring to FIG. 4B, an embodiment similar to that of FIG. 4A is depicted, with exception that a plug member is not utilized. Rather, after the elongate prosthesis has been deployed through retraction of the helical tubular member (50), closure of the defect and hemostasis are achieved merely through the tissue coaptation provided by the helically deployed elongate prosthesis, which preferably has a unloaded three dimensional helical size that is smaller than that of the helical tubular member, resulting in constriction of the elongate prosthesis once deployed and free of the helical tubular member (54).

Figure 4C:
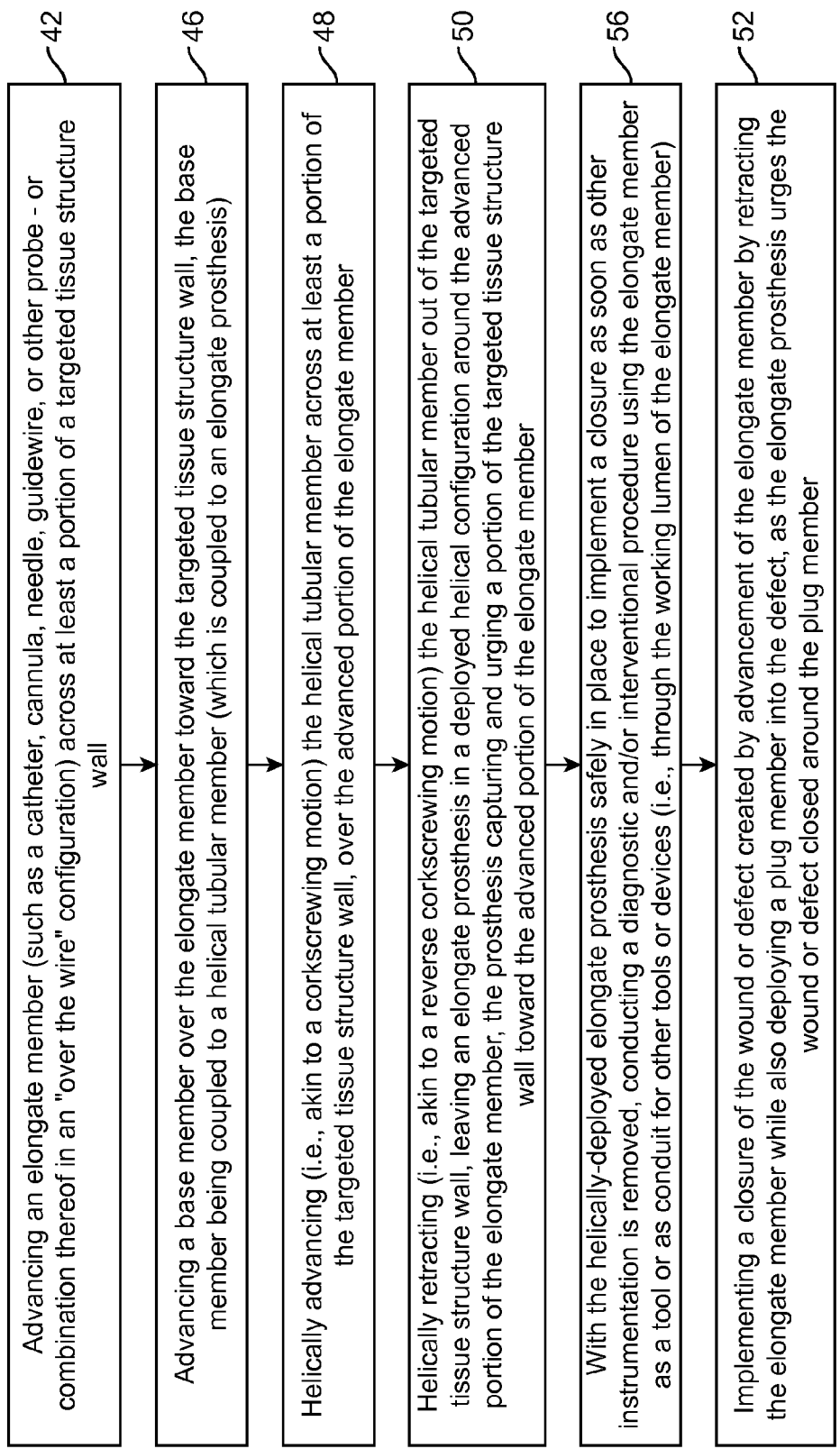

Referring to FIG. 4C, an embodiment is shown wherein the elongate prosthesis member is helically deployed around the installed elongate member (steps 42, 46, 48, and 50) before any diagnostic and/or interventional procedure is conducted (56). This allows for an operator or surgeon to have the confidence that the closure mechanism is safely in place before conducting the diagnostic and/or interventional steps. Subsequently the diagnostic and/or interventional tools are retracted, and retraction of the elongate member and deployment of a plug member results in closure and hemostasis (52).

Figure 4D:
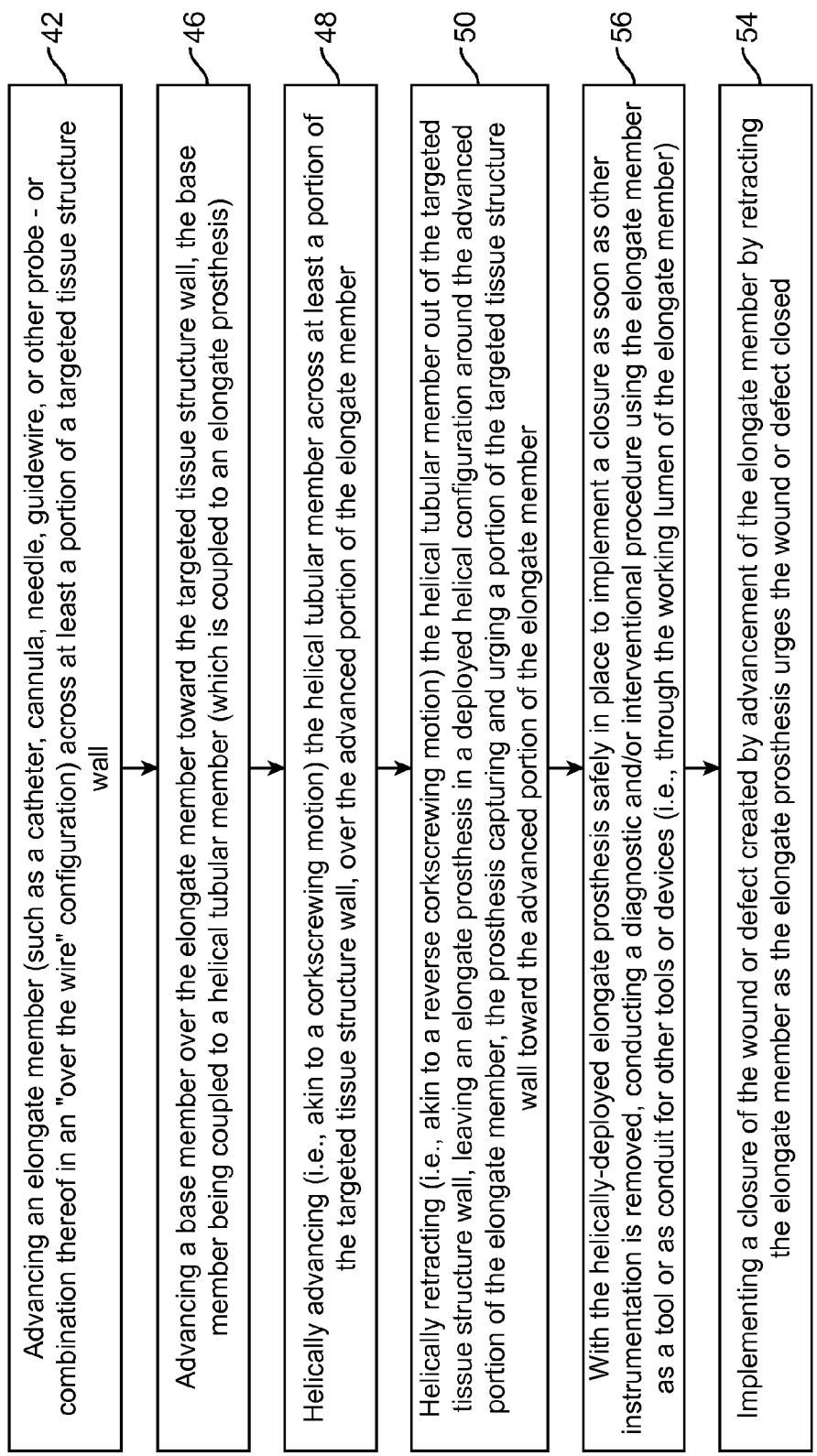

FIG. 4D illustrates an embodiment similar to that described in reference to FIG. 4C, with exception that a plug member is not used, in an analogous scenario to that of FIG. 4B.

Any of the aforementioned deployed structures, including sutures, anchor members, and ratcheting closure device assembly components, may comprise resorbable materials in addition to the aforementioned nonresorbable materials—to facilitate combinations and permutations which may be completely resorbed, leaving behind a biologically healed transapical access wound.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject interventions may be provided in packaged combination for use in executing such interventions. These supply "kits" further may include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally know or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A system for creating and sealing a defect in a tissue wall, comprising:
   a. an elongate guiding member configured to be advanced across the tissue wall, creating the defect in the tissue wall;

b. a base member having a proximal end and a distal end, the proximal end being configured to be manually manipulated by an operator;

c. a helical tubular member having a proximal end, a distal end, a longitudinal axis, and a helical length in between the proximal and distal ends, the helical tubular member defining a helical lumen therethrough, wherein the proximal end is coupled to the base member and the distal end defines a distal outlet of the helical lumen;

d. an elongate prosthesis coupled to the helical tubular member along two or more portions of the helical length and configured to be deployed into a portion of the tissue wall when decoupled from the helical tubular member, wherein the helical tubular member and elongate prosthesis are configured to be helically advanced together into an advanced position in the tissue wall with the defect substantially concentric with the longitudinal axis of the elongate guiding member, and to decouple upon helical retraction, leaving the elongate prosthesis behind in a deployed helical configuration similar to that previously defined by the helical advanced position of the helical tubular member and elongate prosthesis;

e. an asymmetric prosthetic plug member having a proximal end, an elongate central portion, and a distal end, the prosthetic plug member configured to be permanently implantable into the defect in the tissue wall and configured to span at least a portion of a depth dimension of the defect in the tissue wall and place at least a portion of the tissue wall adjacent the defect into a constrained configuration in between the plug member and portions of the deployed helical configuration of the elongate prosthesis such that coaptation of the tissue from the elongate prosthesis constricts the tissue towards the prosthetic plug member, biasing the prosthetic plug member to move proximally, causing the distal plug end to seal the defect; and f. a catheter member configured to be advanced across the tissue wall guided by the elongate guiding member, the catheter member being configured to create a tissue defect during advancement and to allow passage of at least one tool across the tissue wall, wherein the base member is movably coupled to the catheter member via an annulus created through the base member such that the base member is configured to be helically advanced relative to the catheter member, and wherein the proximal end of the helical tubular member is fixed relative to the base member.

2. The system of claim 1, wherein the base member comprises an elongate shaft.

3. The system of claim 1, wherein the base member defines a hole therethrough, the hole configured to facilitate a movable coupling between the base member and an elongate instrument selected from the group consisting of: a catheter, a cannula, a dilator, a needle, a guidewire, and an elongate probe.

4. The system of claim 1, wherein the helical tubular member has a tubular outer diameter between about 2 mm and about 25 mm.

5. The system of claim 1, wherein the helical tubular member has a helical lumen diameter between about 10 thousandths of an inch and about 80 thousandths of an inch.

6. The system of claim 1, wherein the helical tubular member has a helical winding pitch between about 1 mm and about 10 mm.

7. The system of claim 1, wherein the helical tubular member distal end comprises a cutting tip.

8. The system of claim 1, wherein the helical tubular member comprises a metal or polymer material.

9. The system of claim 8, wherein the helical tubular member comprises a helically-bent section of metal hypotube.

10. The system of claim 1, wherein the elongate prosthesis comprises an unloaded three dimensional shape that is different from the shape of the helical lumen.

11. The system of claim 10, wherein the unloaded three dimensional shape substantially approximates a line.

12. The system of claim 10, wherein the unloaded three dimensional shape comprises a helical shape having a circular section diameter that is less than that of the helical lumen.

13. The system of claim 10, wherein the elongate prosthesis is highly flexible into a plurality of unloaded three dimensional shape configurations.

14. The system of claim 13, wherein the elongate prosthesis comprises an element selected from the group consisting of: a suture, a wire, and a linkage.

15. The system of claim 1, wherein the elongate prosthesis comprises a material selected from the group consisting of: a metal, a non-bioresorbable polymer, a bioresorbable polymer, a non-bioresorbable co-polymer, and a bioresorbable co-polymer.

16. The system of claim 1, wherein the plug member comprises a distal portion coupled to the distal end of the central portion, and a proximal portion coupled to the proximal end of the central portion, each of the proximal and distal portions being expandable from a collapsed configuration to an expanded configuration such that the outer diameter of each collapsed configuration is larger than that of the central portion.

17. The system of claim 16, wherein the plug member comprises a material selected from the group consisting of: a metal, a non-bioresorbable polymer, a bioresorbable polymer, a non-bioresorbable co-polymer, a bioresorbable co-polymer, and a fabric.

18. The system of claim 1, wherein the prosthetic plug member central portion comprises a substantially cylindrical geometry.

19. The system of claim 1, wherein the catheter member defines a working lumen therethrough, the working lumen configured to allow passage of at least one tool across the tissue wall.

20. The system of claim 19, wherein the working lumen is configured to accommodate passage of a surgical tool or implant.

21. The system of claim 20, wherein the catheter member comprises a hemostatic valve configured to enable passage of the surgical tool or implant while preventing blood loss through the working lumen of the catheter member.

22. The system of claim 1, wherein the guiding member comprises a guide wire having an outer diameter.

23. The system of claim 1, further comprising:
a needle;
a guide wire; and
a dilator member;
wherein the guiding member is configured to be advanced by successive placement of the needle, the guide wire, the dilator member, and the catheter member.

24. The system of claim 23, wherein the catheter member is configured to be advanced across the tissue wall following the path of the guiding member.

25. The system of claim 23, wherein the dilator member is configured to be advanced across the tissue wall following the path of the guiding member.

26. The system of claim 23, wherein the catheter member is configured to be advanced across the tissue wall following the path of the dilator member.

* * * * *